(12) United States Patent
Zhou et al.

(10) Patent No.: US 8,065,004 B2
(45) Date of Patent: Nov. 22, 2011

(54) METHOD AND APPARATUS FOR AUTOMATIC SELF-TEST OF MEDICAL DEVICE

(75) Inventors: Saixin Zhou, Shenzhen (CN); Min An, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 503 days.

(21) Appl. No.: 11/876,135

(22) Filed: Oct. 22, 2007

(65) Prior Publication Data

US 2008/0147136 A1     Jun. 19, 2008

(30) Foreign Application Priority Data

Dec. 18, 2006 (CN) .......................... 2006 1 0157675

(51) Int. Cl.
*A61N 1/08* (2006.01)
(52) U.S. Cl. ............................................. 607/27; 607/5
(58) Field of Classification Search ................ 607/5, 16, 607/27, 31; 324/426
See application file for complete search history.

(56) References Cited

U.S. PATENT DOCUMENTS

| | | | | |
|---|---|---|---|---|
| 5,579,234 | A | * | 11/1996 | Wiley et al. .................. 702/118 |
| 5,899,925 | A | * | 5/1999 | Ochs et al. ........................ 607/5 |
| 6,329,822 | B1 | | 12/2001 | Powers |
| 6,988,012 | B2 | | 1/2006 | Renz |

FOREIGN PATENT DOCUMENTS

| | | |
|---|---|---|
| CN | 1220133 A | 9/1999 |
| CN | 1382417 | 12/2002 |
| WO | WO 80/02498 | 11/1980 |

OTHER PUBLICATIONS

Wu Jianhua, "Magnetic resonance self-protection fault error repair," Chinese Medical Equipment Journal, Feb. 2007, pp. 91-92 (includes abstract page).

Tang Hongqi, "Commander brand monitor self-check program calls and adjustment," Chinese Journal of Medical Instrumentation, Feb. 1997, p. 122 (includes abstract page).

\* cited by examiner

*Primary Examiner* — Kennedy Schaetzle
*Assistant Examiner* — Erica Lee
(74) *Attorney, Agent, or Firm* — Kory D. Christensen; Stoel Rives LLP

(57) ABSTRACT

A method and apparatus are disclosed for automatic self-test of a medical device. The method includes detecting whether the medical device has reached an automatic self-test time set in the last time, when the medical device is in a power-off state. If the result of the detecting is affirmative, the method includes initiating the medical device to perform automatic self-test according to determined automatic self-test items, and determining the automatic self-test time of the next time for the medical device based on the result of the automatic self-test. The automatic self-test time and the automatic self-test items are relatively flexible so as to avoid the unnecessary consumption of electricity and the unnecessary wear-and-tear of the instrument caused by unnecessary automatic self-test.

6 Claims, 2 Drawing Sheets

Fig. 2

METHOD AND APPARATUS FOR AUTOMATIC SELF-TEST OF MEDICAL DEVICE

TECHNICAL FIELD

The present invention relates to a medical device in the medical area, and in particular, to a method and apparatus for automatic self-test of a defibrillator.

BACKGROUND ART

A defibrillator is not a frequently used medical device, which performs the functions of defibrillation, pace making, supervision, etc. In addition to ordinary supervision functions, it can further perform defibrillation and pace making for curing serious diseases, such as ventricular fibrillation, atrial fibrillation, bradycardia, etc.; therefore, it is also a first aid instrument and thus the reliability requirements thereon are much higher than those on other ordinary medical devices. Therefore, in addition to improving the reliability of the design of the instrument, an automatic self-test mechanism is further expected. A block diagram of an existing defibrillator is shown in FIG. 1.

There are mainly two automatic self-test methods of the existing defibrillator.

One is to perform an automatic self-test at powering-on of the instrument, but no automatic self-test at power-off. It is possible for the defibrillator to be in the powering-off state most of the time because it is a scarcely used instrument, and problems cannot be discovered in time because the automatic self-test cannot be performed in the power-off state. The first aid time may be delayed if any problem is discovered at the time of using the instrument, even causing the instrument to be unusable and bringing about danger to the lives of patients. Furthermore, performing an automatic self-test in the powering-on procedure of the instrument may delay the time of powering on, thereby the first aid time of the patients may also be delayed, and the success rate of first aid may be influenced accordingly.

Another is to perform partial automatic self-test at turning-on of the instrument and to perform periodical automatic self-testing during the power-off of the instrument. The method of performing periodical automatic self-testing at power-off is not sufficiently flexible. For example, any automatic self-test will consume a certain electrical capacity of the battery, and thus unnecessary automatic self-testing may consume excessive electricity, which is very important for those first aid instruments, such as the defibrillator. Furthermore, the time of using the defibrillator by the users may be in conflict with the set time of the periodical automatic self-test, thus making the automatic self-test impossible to be realized and problems impossible to be discovered. If it is necessary for the defibrillator to be used for a long time from 10 PM to 6 PM of the next day, but the automatic self-test time is set at 3 AM, it may make the automatic self test impossible to be performed.

SUMMARY OF THE INVENTION

Taking consideration of the above problem, an object of the present invention is to provide a method and apparatus for automatic self-test, which makes a medical device to perform automatic detecting flexibly and efficiently, thereby the normal operation of the medical device can be guaranteed.

In order to achieve the above object, the present invention provides a method for automatic self-test of a medical device, comprising the steps of:

detecting whether the medical device has reached an automatic self-test time set in the last time, when the medical device is in a power-off state;

initiating the medical device to perform automatic self-test, according to determined automatic self-test items, if the result of the detecting is affirmative; and determining the automatic self-test time of the next time for the medical device based on the result of the automatic self-test.

In order to achieve the above object, the present invention provides an apparatus for automatic self-test of a medical device, comprising:

a detecting unit, for detecting whether the medical device has reached an automatic self-test time set in the last time, when the medical device is in a power-off state;

an initiating unit, for initiating the medical device to perform automatic self-test, according to determined automatic self-test items, if the result of the detecting is affirmative; and a determining unit, for determining the automatic self-test time of the next time for the medical device based on the result of the automatic self-test.

The advantageous effects of the present invention include the following. 1) The present invention may determine the automatic self-test time of the next time after the medical device is used or based on the result of this automatic self-test after each automatic self-test, such that the automatic self-test time is relatively flexible, and the automatic self-test can be performed more effectively. At the same time, the unnecessary consumption of electricity and the unnecessary wear and tear of the medical device caused by unnecessary and too frequent automatic self-tests, and the problems caused by too long of an interval between automatic self-tests can be avoided. In addition, the conflict between the use time and the set periodical automatic self-test time can be avoided as well. 2) The items of each automatic self-test of the present invention are also flexible, such that all items of the medical device are classified according to their frequencies of usage and importance. The automatic self-test frequencies of the items of basic and important functions are high, while the automatic self-test frequencies of the infrequently used and not important functions are low. Therefore, the unnecessary consumption of the electricity and the unnecessary wear-and-tear of medical device caused by automatic self-test can be avoided.

BRIEF DESCRIPTION OF DRAWINGS

The features and advantages of the present invention will be described in detail in the following embodiments with reference to the accompanying drawings, wherein.

BEST MODE OF CARRYING OUT THE INVENTION

The following is a description of a method and apparatus for an automatic self-test of a medical device of the present invention, taking the defibrillator as an example of the medical device and with reference to the accompanying drawings.

Figure 1:
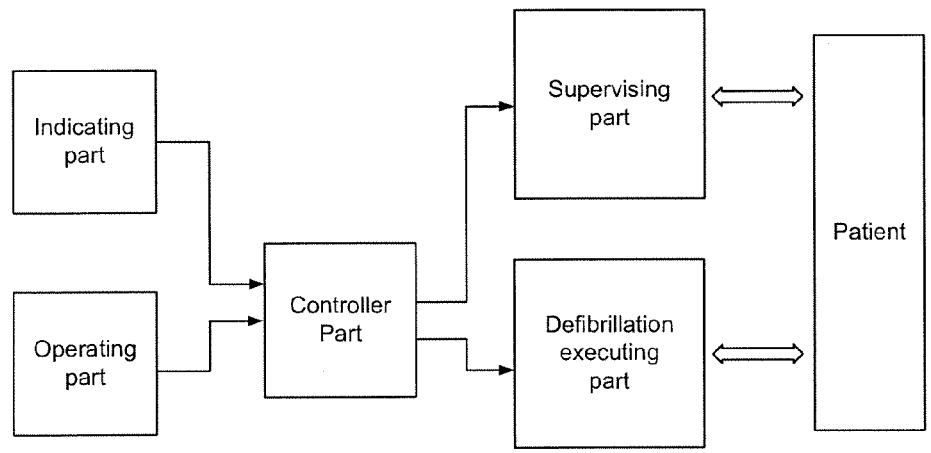
FIG. 1 is a block diagram showing the structure of an existing defibrillator.
Figure 2:
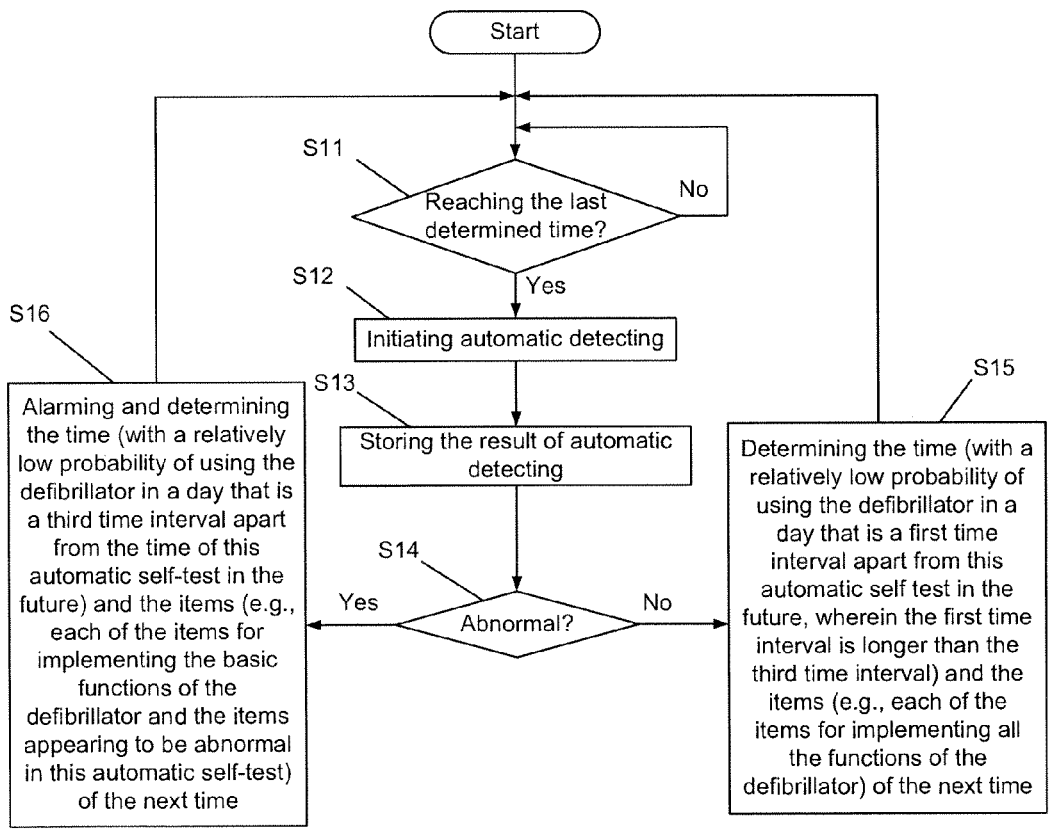
FIG. 2 is a flowchart of a method for automatic self-test of the defibrillator, according to a first embodiment of the present invention.

FIG. 2 is a flowchart showing method for automatic self-test of a defibrillator, according to a first embodiment of the present invention. As shown in FIG. 2, at step S11, when the defibrillator is in its power-off state, it is detected whether the automatic self-test time determined in the last time has arrived.

If the detected result at step S11 indicates that the defibrillator in the power-off state does not reach the automatic self-test time determined in the last time, the procedure goes back to step S11 for detecting continuously.

If the detected result at step S11 indicates that the defibrillator in the power-off state has reached the automatic self-test time determined in the last time, then at step S12, the defibrillator is initiated to perform automatic self-test, according to automatic self-test items determined in the last time.

Then at step S13, the result of the automatic self-test of the defibrillator is stored. At step S14, it is judged whether there is any abnormal item in the defibrillator based on the result of automatic self-test.

If the result of the automatic self-test indicates that there are abnormal items in the defibrillator, then at step S16, an alarm is set. At the same time, a time interval with relatively low probability of using the defibrillator in a day that is a third time interval apart from the time of this automatic self-test in the future is set to the automatic self-test time of the next time, and the automatic self-test items of the next time are determined. Wherein, the time interval, with relatively low probability of using the defibrillator, may be determined based on the time intervals in a day recorded in the most recent N times, in which the defibrillator is used by users, to thereby keep away as far as possible the time interval of automatic self-test from those times of using the defibrillator by the users. And wherein the automatic self-test items of the next time may be, for example, each of the items for implementing the basic functions of the defibrillator and the items appearing to be abnormal in this automatic self-test. Then the procedure returns to step S11 to continue detecting.

If the result of the automatic self-test indicates that the defibrillator is normal, then at step S15, a time interval with relatively low probability of using the defibrillator in a day that is a first time interval apart from the time of this automatic self-test in the future is set to the automatic self-test time of the next time, wherein the first time interval is longer than the third time interval. Also at step S15, the automatic self-test items of the next time are determined, wherein the automatic self-test items of the next time may be, for example, each of the items for implementing all the functions of the defibrillator. Then the procedure returns to step S11 to continue detecting.

In the first embodiment above, the first time interval, the third time interval and N can be chosen according to practical requirements. For example, the first time interval is three days, the third time interval is 24 hours, and N is 100 times.

In the first embodiment above, the automatic self-test time and the automatic self-test items of the next time are determined after each automatic self-test; however, the present invention is not limited to this. According to the present invention, it is also possible for the automatic self-test time and automatic self-test items of the next time to be determined after each time that the defibrillator is used.

Figure 3:
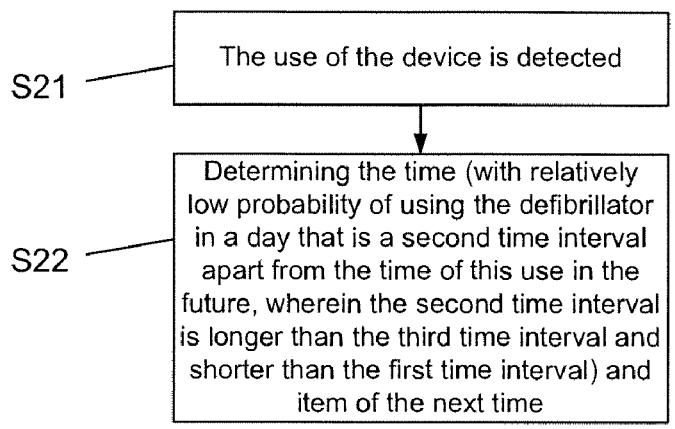
FIG. 3 is a flowchart of a method for determination of the next automatic self-test time and the next automatic self-test items after using the defibrillator, according to a second embodiment of the present invention.

FIG. 3 is a flowchart showing a method for the determination of the automatic self-test time and the automatic self-test items of the next time after using the defibrillator, according to a second embodiment of the present invention. As shown in FIG. 3, the use of the defibrillator by the user is detected at step S21. Then, at step S22, after the completion of the use of the defibrillator, a time interval with relatively low probability of using the defibrillator in a day that is a second time interval apart from the time of this use in the future is set to the automatic self-test time of the next time, wherein the second time interval is longer than the third time interval and shorter than the first time interval. Also at step S22, the automatic self-test items of the next time are determined based on the result of the last automatic self-test. When the result of the last automatic self-test indicates that there are abnormal items in the defibrillator, the automatic self-test items of the next time may, for example, be each of the items for implementing the basic functions of the defibrillator and those abnormal items of the last automatic self-test. When the result of the last automatic self-test indicates that the defibrillator is normal, the automatic self-test items of the next time may, for example, be each of the items for implementing the basic and important functions of the defibrillator or each of the items for implementing all the functions of the defibrillator.

Figure 4:
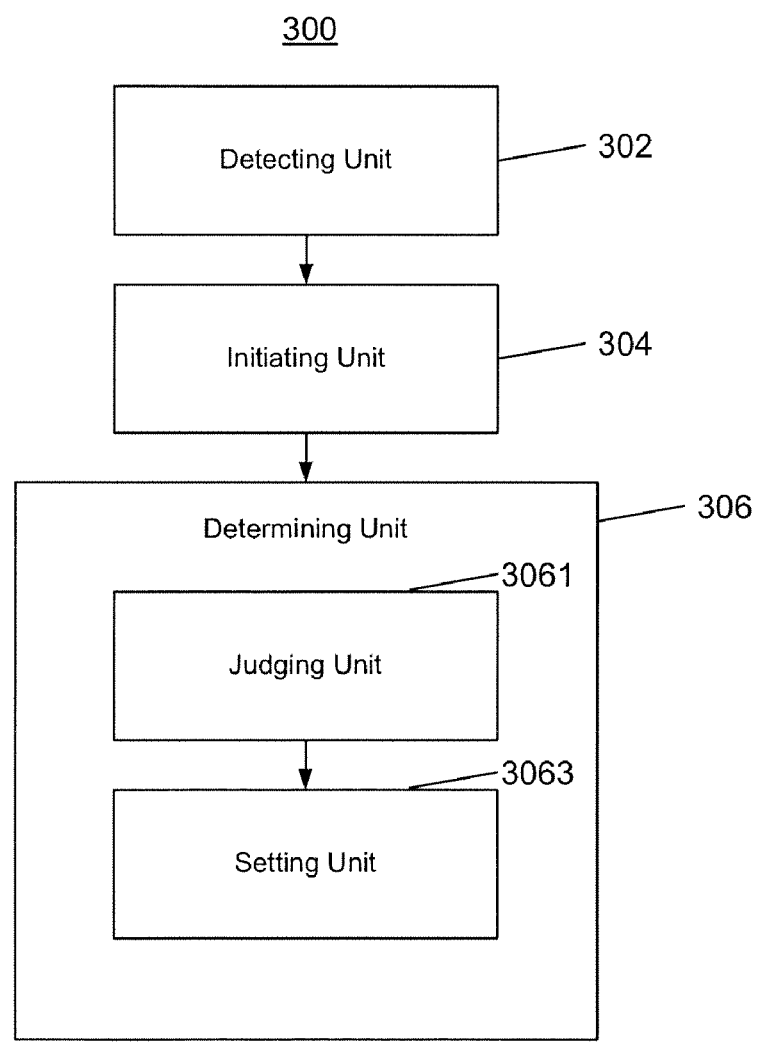
FIG. 4 is a schematic diagram showing an apparatus for automatic self-test of a defibrillator, according to an embodiment of the present invention.

FIG. 4 is a schematic diagram showing an apparatus for automatic self-test of the defibrillator according to an embodiment of the present invention. As shown in FIG. 4, an apparatus 300 for automatic self-test of the defibrillator comprises: a detecting unit 302 for detecting whether the defibrillator has reached the automatic self-test time set in the last time, when the defibrillator is in a power-off state; an initiating unit 304 for initiating the defibrillator to perform automatic self-test, according to determined automatic self-test items, when the result of the detecting is affirmative; and a determining unit 306 for determining the automatic self-test time and automatic self-test items of the next time based on the result of automatic self-test, or for determining the next automatic self-test time and the next automatic self-test items after the defibrillator is used.

Wherein the determining unit 306 further comprises: a judging unit 3061 for judging whether there is any abnormal item in the defibrillator based on the result of the automatic self-test; and a setting unit 3063 for, when the result of the judging is negative, setting a time interval with relatively low probability of using the defibrillator in a day that is a first time interval apart from the time of this automatic self-test in the future as the automatic self-test time of the next time, and setting all the items of the defibrillator as the automatic self-test items of the next time. When the result of the judging is affirmative, the setting unit 3063 sets a time interval with relatively low probability of using the defibrillation in a day that is a third time interval apart from the time of this automatic self-test in the future as the automatic self-test time of the next time, wherein the third time interval is shorter than said first time, and sets items for implementing the basic functions of the defibrillator and those abnormal items of this automatic self-test as the automatic self-test items of the next time.

In addition, the judging unit 3061 further judges whether there is any abnormal item in the defibrillator, based on the result of the last automatic self-test after the defibrillator is used. After the defibrillator is used, the setting unit 3063 further sets a time interval, with relatively low probability of using the defibrillator in a day that is a second time interval apart from the last automatic self-test time in the future as the automatic self-test time of the next time, and sets items for implementing the basic functions and important functions of the defibrillator as the automatic self-test items of the next time when the result of the judging is negative. Otherwise, the setting unit 3063 sets items for implementing the basic functions of the defibrillator and those abnormal items in the last automatic self-test as the automatic self-test items of the next time.

Wherein, in the present embodiment, the second time interval is longer than the third time interval but shorter than the first time interval. In addition, the time interval with relatively high probability of not using the defibrillator in a day is determined based on time intervals in a day recorded in the most recent N in which the defibrillator is used, and it is set as the time interval with relatively low probability of using the defibrillator, so that the automatic self-test time may keep clear of the time intervals of using the defibrillator, as far as possible.

In the above embodiment, the time interval with relatively low probability of using the defibrillator is the time interval with relatively high probability of not using the defibrillator in a day that is determined based on the time interval in a day recorded in the most recent N times in which the defibrillator is used, but the present invention is not limited to this. In the present invention, the time interval with relatively high probability of not using the defibrillator may also be determined based on time intervals in a day recorded in the most recent N in which the defibrillation is not used, and is set as the time interval with relatively low probability of using the defibrillator.

In the above embodiments, items for implementing the basic functions of the defibrillator and items for implementing the important functions of the defibrillator are set according to the frequency of use and importance of each of the items.

In the above embodiments, at the same time of determining the automatic self-test time of the next time for the defibrillator, the automatic self-test items of the next time are also determined; however, the present invention is not limited to this. In the present invention, the automatic self-test items of each time may also be set to the same and fixed items, which are determined in advance. Thereby, only the automatic self-test time of the next time for the defibrillator is determined each time, and it is not necessary for the automatic self-test items of the next time to be determined.

In addition, although in the above embodiments the defibrillator is taken as an example to describe method and apparatus for automatic self-test according to the present invention, method and apparatus for automatic self-test according to the present invention are not limited to be used in the defibrillator. It may also be used in other medical devices.

It shall be understood by those skilled in the art that various variations and modifications can be made on the method and apparatus for automatic self-test disclosed in the present invention without departing from the substance of the present invention. Therefore, the scope of the present invention is defined by the attached claims.

What is claimed is:

1. A method for automatic self-test of a medical device comprising the steps of:
   detecting whether the medical device has reached an automatic self-test time set in a last time, when the medical device is in a power-off state;
   initiating the medical device to perform an automatic self-test according to determined automatic self-test items, if the result of the detecting is affirmative;
   detecting the result of the automatic self-test;
   judging whether there is any abnormal item in the medical device based on the results of the automatic self-test;
   determining the automatic self-test time of a next time for the medical device based on the result of the automatic self-test, wherein determining the automatic self-test time of the next time comprises setting a time interval with relatively low probability of using the medical device in a day that is a first time interval apart from the time of the current automatic self-test in the future as the automatic self-test time of the next time, if the result of the judging is negative; and
   determining the automatic self-test items of the next time for the medical device based on the result of the automatic self-test,
      wherein determining the automatic self-test items comprises setting all available automatic self-test items in the medical device as the automatic self-test items of the next time, if the result of the judging is negative, and
      wherein determining the automatic self-test items comprises setting a sub-group of automatic self-test items corresponding to frequently used functions of the medical device as the automatic self-test items of the next time, if the result of the judging is affirmative.

2. The method according to claim 1, further comprising:
   setting a time interval with relatively low probability of using the medical device in a day that is a third time interval apart from the time of the current automatic self-test in the future as the automatic self-test time of the next time, if the result of the judging is affirmative, wherein the third time interval is shorter than the first time interval.

3. The method according to claim 1, wherein the time interval with relatively low probability of using the medical device is a time interval in a day with relative high probability of not using the medical device that is determined based on time intervals in a day for most recent predetermined times in which the medical device is used.

4. The method according to claim 1, wherein the time interval with relatively low probability of using the medical device is a time interval in a day with relatively high probability of not using the medical device that is determined based on time intervals in a day for most recent predetermined times in which the medical device is not used.

5. The method according to claim 1, wherein the medical device comprises a defibrillator.

6. A method for automatic self-test of a medical device comprising:
   detecting whether the medical device has reached an automatic self-test time set in a last time, when the medical device is in a power-off state;
   classifying the available automatic self-test items in the medical device into at least a first group of items and a second group of items, wherein the classification is based at least in part on frequency of using the corresponding functions of the medical device;
   initiating the medical device to perform an automatic self-test according to determined automatic self-test items, if the result of the detecting is affirmative;
   detecting the result of the automatic self-test;
   judging whether there is any abnormal item in the medical device based on the results of the automatic self-test;
   determining the automatic self-test time of a next time for the medical device based on the result of the automatic self-test, wherein determining the automatic self-test time of the next time comprises setting a time interval with relatively low probability of using the medical device in a day that is a first time interval apart from the time of the current automatic self-test in the future as the automatic self-test time of the next time, if the result of the judging is negative; and determining the automatic self-test items of the next time for the medical device after the medical device is used, wherein determining the automatic self-test items comprises:

setting the first group of items and the second group of items of the medical device as the automatic self-test items of the next time, if the result of the judging is negative; and setting the first group of items of the medical device and abnormal items in the last automatic self-test as the automatic self-test items of the next time, wherein the first group of items corresponds to frequently used functions of the medical device, if the result of the judging is affirmative.

* * * * *